United States Patent [19]

Jacobson et al.

[11] Patent Number: 5,015,461
[45] Date of Patent: May 14, 1991

[54] NOVEL HIGH SURFACE AREA OXIDE COMPOSITIONS WITH A PYROCHLORE STRUCTURE, METHODS FOR THEIR PREPARATION, AND CONVERSION PROCESSES UTILIZING SAME

[75] Inventors: Allan J. Jacobson, Princeton; Richard B. Hall, Warren; Charles A. Mims, Summit; Joseph T. Lewandowski, Whitehouse Station, all of N.J.

[73] Assignee: Exxon Research & Engineering Company, Florham Park, N.J.

[21] Appl. No.: 343,752

[22] Filed: Jun. 26, 1989

[51] Int. Cl.$^5$ .................... C01G 33/00; C01G 35/00
[52] U.S. Cl. .................................... 423/593; 502/324; 502/340; 502/349; 502/353
[58] Field of Search ............. 423/593, 62, 65; 502/340, 349, 353, 324

[56] References Cited

U.S. PATENT DOCUMENTS 4,678,505 7/1987 Bushey ........................... 423/592

FOREIGN PATENT DOCUMENTS 455915 7/1975 U.S.S.R. ........................ 423/593
1181999 9/1985 U.S.S.R. ........................ 423/593
1115565 5/1968 United Kingdom ............. 423/593

OTHER PUBLICATIONS

"Crystal Chemistry of Pyrochlores", Jr. Amer. Ceramic Soc., vol. 45, No 1, 1962, by Aleshin, et al. pp. 18-25.

Primary Examiner—Gary P. Straub
Assistant Examiner—Steven Bos
Attorney, Agent, or Firm—Jay Simon

[57] ABSTRACT

Processes for the conversion of hydrocarbons, and most preferably methane, to higher hydrocarbons and olefins are disclosed, including contacting the hydrocarbons with a mixed metal oxide catalyst having the pyrochlore structure. Preferably, these catalysts have the general formula $A_nB_2O_7\text{-}x$, where A can be various mono-, di-, and trivalent metal cations, B can be various tri-, tetra-, penta-, and hexavalent metal cations, $0 \leq n \leq 2.0$, and $0 \leq x \leq 1.0$. Novel, high surface area, mixed metal oxide cataysts having the pyrochlore structure are also disclosed, including those having the formula $A_2B_2O_7$, where A is divalent and B is niobium and/or tantalum, and those having the formula $A_2(Sn_{2\text{-}y}A_y)O_{7\text{-}z}$, where A is bismuth and/or lead, $0.0 \leq y \leq 1.0$, and $0.0 \leq z \leq 1.0$.

7 Claims, No Drawings

NOVEL HIGH SURFACE AREA OXIDE COMPOSITIONS WITH A PYROCHLORE STRUCTURE, METHODS FOR THEIR PREPARATION, AND CONVERSION PROCESSES UTILIZING SAME

FIELD OF THE INVENTION

The present invention relates to the conversion of light hydrocarbons to higher hydrocarbons and olefins. More particularly, the present invention relates to the direct conversion of methane to higher hydrocarbons. Still more particularly, the present invention relates to novel high surface area oxide compositions with the pyrochlore structure. Still more particularly, the present invention relates to the use of these high surface area oxide compositions as catalysts for hydrocarbon conversion processes.

BACKGROUND OF THE INVENTION

As the interest in natural gas as a source of hydrocarbons has risen, the desirability of converting methane, the major element of natural gas, into more easily handled products, such as olefins, aromatics and higher hydrocarbons, has greatly increased. Various processes exist for converting methane into such hydrocarbons, but processes for the direct conversion of methane into light olefins and higher hydrocarbons would be highly useful. Such processes, however, have required special catalysts which can affect such conversion.

For example, according to Burch et al, "Comparative Study of Catalysts for the Oxidative Coupling of Methane;" Applied Catalysts, 43 (1988), pp. 105-116, various oxides are disclosed as catalysts for methane coupling, and, in fact, comparison is made in this article of various such oxide materials in terms of activity and selectivity, including magnesium oxide and various mixed oxides, including alkali metals which are said to alter the product distribution obtained therewith. According to Otsuka, "Direct Conversion of Methane to Higher Hydrocarbons," Sekiyu Gakkaishi, Vol. 30, No. 6, 1987, pp. 385-396, the rare earth metal oxides are disclosed for such direct conversion processes. Furthermore, the addition of alkali metals and in particular alkali metal halides such as LiCl is said to enhance the selectivity of these processes for the production of ethane. The lanthanide oxides are particularly described in this article. In Sofranko et al, "The Oxidative Conversion of Methane to Higher Hydrocarbons," Journal of Catalysis, Vol. 103 (1987), pp. 1-9, there is a further disclosure of transition metal oxides for use in these processes, including manganese, indium, germanium, antimony, tin, bismuth, and lead oxides, as coupling catalysts which give from 10 to 50% selectivity to higher hydrocarbons, including the use of a silica support therefor.

A large class of ternary oxides having the general formula $A_2B_2O_7$, where A and B are metals, are known to adopt the structure of the natural mineral pyrochlore, $(Na,Ca)(Nb,Ta)_2O_6(OH,F)$. Subramanian et al, Prog. Solid St. Chem., 15, 55-143 (1983), have comprehensively reviewed the field of pyrochlore compounds, including the use of these materials in various electrical processes. The Subramanian et al article thus discloses that pyrochlore oxides are normally made by reaction of the constituent oxides at high temperatures, usually greater than about 800 C. Typically, the products produced thereby have low surface area and comprise crystals which are about 10 microns and up, and which have surface areas of less than about 1 $m^2/g$. Compositions with low surface area are usually not effective catalysts.

U.S. Pat. No. 4,124,539 discloses lead enriched pyrochlore compounds which contain ruthenium, iridium and mixtures thereof. The compositions are prepared by solid state reaction of a lead source and a ruthenium and/or an iridium source at temperatures below about 600° C. in an oxygen environment. The '539 patent discloses that the compositions have a surface area of about 9 $m^2/g$, and the patent states that they have application in electrochemical processes, such as electrocatalysis.

U.S. Pat. No. 4,163,706 discloses bismuthrich pyrochlore-type compounds for use in the same types of processes. This material, however, was said to have a surface area of 178 $m^2/g$.

U.S. Pat. No. 4,129,525 also discloses lead-enriched and bismuth-enriched pyrochlore compounds which contain ruthenium, iridium and mixtures thereof. The pyrochlore oxides are prepared by reaction of lead and/or bismuth cations with ruthenium and/or iridium cations in aqueous solution. The pyrochlore oxide is precipitated from a liquid alkaline medium having a pH of about 13.5 in an oxygen environment at a temperature below about 200° C. The reaction conditions provide a product with a high surface area, i.e., around 60-250 $m^2/g$. In a similar vein are U.S. Pat. Nos. 4,146,458, relating to such pyrochlore compounds containing Ru, Rh, Ir, Os, Pt, Ru-Pb, and Ir-Pb mixtures; and 4,192,780, relating to methods of preparing pyrochlore compounds by the precipitation of the metal cations from an aqueous solution in a liquid alkaline medium in the presence of an oxygen source at below 200° C., resulting in compounds of 25-150 $m^2/g$ surface area, which is said to be generally useful in a catalytic or electrocatalytic environment. Similar disclosures are included in U.S. Pat. Nos. 4,203,871; 4,225,469; 4,434,031; and 4,440,670.

While moderate selectivities and conversions have been obtained with these oxides, there has been a significant need for improved catalysts for direct methane conversion.

SUMMARY OF THE INVENTION

In accordance with the present invention, the need to provide effective catalysts for oxidative methane conversion to higher hydrocarbons and other objectives have been accomplished by the invention of a process for the conversion of light hydrocarbons to higher hydrocarbons and olefins which includes contacting such light hydrocarbons with a catalyst comprising a mixed metal oxide having the pyrochlore structure. In a preferred embodiment the mixed metal oxide has the general formula $A_nB_2O_{7-x}$, in which A can be a mono-, di- and/or trivalent metal cation; B can be a tri-, tetra-, penta- and/or hexavalent metal cation; $0.0 \leq n \leq 2.0$; and $0.0 \leq x \leq 1.0$.

In accordance with a preferred embodiment of the process of the present invention, the process effects the direct conversion of methane to higher hydrocarbons by contacting methane with a catalyst comprising a mixed metal oxide having the pyrochlore structure as set forth above. In one embodiment the process is carried out without the addition of any additional oxidizing agent, and includes intermittently regenerating the catalyst by contacting it with an oxidizing agent, preferably air or oxygen. In another embodiment, however, the process is carried out by contacting methane with the catalyst in the presence of such an oxidizing agent.

In accordance with the present invention novel high surface area oxide compounds with a pyrochlore structure have also now been discovered.

In a preferred embodiment of the compounds of the present invention wherein the pyrochlore compound has the formula $A_2B_2O_7$, the metal cation A is a divalent metal cation selected from the group consisting of lead, calcium and mixtures thereof, and B is a metal cation selected from the group consisting of niobium, tantalum and mixtures thereof.

In a preferred embodiment of the compounds of the present invention, the novel high surface area oxide compounds with a pyrochlore structure have the formula $A_2(Sn_{2-y}A_y)O_{7-z}$, in which A is bismuth and/or lead, $0.0 \leq y \leq 1.0$; and $0.0 \leq z \leq 1.0$. Preferably, the high surface area oxide compounds hereof have a surface area greater than about 20 m²/g, and most preferably greater than about 100 m²/g.

DETAILED DESCRIPTION

One aspect of the present invention is based upon the unexpected discovery that certain mixed metal oxides having the pyrochlore structure are surprisingly effective catalysts for the conversion of light hydrocarbons to higher hydrocarbons and olefins, and most particularly for the direct conversion of methane to higher hydrocarbons and olefins therewith. Thus, in these processes hydrocarbon feedstocks, preferably together with a gaseous oxidizing agent, are contacted with these active catalytic materials to produce higher hydrocarbons or olefins, plus hydrogen and water. In an alternative process, however, these processes may be effected without the addition of a separate gaseous oxidizing agent, in which case the oxygen for the oxidation process is supplied by the solid catalyst itself. Therefore, in the latter case the catalyst should be periodically reoxidized back to an active state by separate contact with an oxidizing agent in the absence of the hydrocarbon feed stream for subsequent use therein.

An important element in the process of the present invention is based upon the nature of the mixed metal oxides having the pyrochlore structure which are used therein. These are mixed metal oxides which have the general formula $A_nB_2O_{7-x}$ in which A is generally a mono-, di- and/or trivalent metal cation; B is generally a tri-, tetra-, penta- and/or hexavalent cation; $0.0 \leq n \leq 2.0$; and $0.0 \leq x \leq 1.0$. A general listing of the potential cations for metal cation A is as follows:

Monovalent Metal Cation A: potassium, rubidium, cesium, silver and thallium;
Divalent Metal Cation A: calcium, strontium, manganese, cadmium, mercury, tin and lead; and
Trivalent Metal Cation A: yttrium, thallium, and bismuth, and the lanthanide series (La to Lu).
The tri-, tetra-, penta- and hexavalent metal cation B of the above formula is as follows:
Trivalent Metal Cation B: scandium, yttrium, chromium, manganese, iron, and gallium;
Tetravalent Metal Cation B: titanium, zirconium, hafnium, vanadium, niobium, molybdenum, ruthenium, osmium, rhenium, iridium, and lead;
Pentavalent Metal Cation B: niobium, tantalum, rhenium, ruthenium, osmium, rhodium, iridium, antimony, and bismuth; and
Hexavalent Metal Cation B: molybdenum, tungsten, and tellurium.

As can be seen, several metal cations are listed in more than one category since they can, of course, occur in more than one valence or oxidation state. For example, bismuth may occur with oxidation states of +3 and +5, thallium with oxidation states of 1 and +3, and ruthenium with oxidation states of +4 and +5. Other such examples exist, and in any single mixed metal oxide catalyst hereof one element may be present in more than one oxidation state, and more than one A or B metal cation may be present with different oxidation states.

With that in mind, the stoichiometric restriction of the choice of A and B metal cations imposed by the formula $A_nB_2O_{7-x}$, and by the usual valences of A and B is given by the formula: $nV_a + 2V_b = 14 - 2x$ where $V_a$ and $V_b$ are the valences of the A and B metal cations, respectively. When, however, more than one A and/or B metal cation is simultaneously present therein, the valence for $V_a$ and/or $V_b$ is calculated as the average valence weighted by the relative amounts of each species present therein. The application of this relationship can be illustrated by the following examples:

| | | | |
|---|---|---|---|
| $Pb_2Nb_2O_7$ | n = 2; | $V_a$ = 2; | $V_b$ = 5; | x = 0 |
| $Pb_2Sn_2O_6$ | n = 2; | $V_a$ = 2; | $V_b$ = 4; | x = 1 |
| $K(NbTe)O_6$ | n = 1; | $V_a$ = 1; | $V_b$ = 5.5; | x = 1 |
| $(KBi)Sn_2O_6$ | n = 2; | $V_a$ = 2; | $V_b$ = 4; | x = 1 |
| $Sm_2Sn_2O_7$ | n = 2; | $V_a$ = 3; | $V_b$ = 4; | x = 0 |
| $(Pb,Bi)(Sn,Nb)O_7$ | n = 2; | $V_a$ = 2.5; | $V_b$ = 4.5; | x = 0 |

In addition, there is yet another restriction on the selection of various combinations of A and B metal cations. More particularly, besides the stoichiometry, this selection process is also restricted by the radii of the A and B metal cations so selected. Thus, these mixed metal oxides can be formed with the pyrochlore structure when the ratio of the radii of A and B metal cations lies between about 1.4 and 2.2. Once again, when more than one A and/or B metal cations are present, then these radii are calculated as the average weighted radii by the relative amounts of each species present therein.

As for the pyrochlore structure itself, whether a particular composition has that structure can be readily determined by X-ray powder diffraction techniques. The ideal pyrochlore structure thus has a cubic unit cell with a cell constant of about 10.0 to 10.8 Angstroms. The symmetry of the ideal cubic unit cell is described by the space group Fd3m (International Tables for Crystallography) which shows in powder diffraction patterns systematic absences other than for h,k,l all odd or all even. In some systems small distortions of the ideal structure occur which tend to reduce the symmetry of the system to lower than cubic. Such systems, however, still contain the A, B and 0 atoms bonded together in the same general manner, that is with the same structural connectivity. The X-ray powder diffraction data calculated for two typical pyrochlore structures, namely $Cd_2Nb_2O_7$ and $Hg_2Nb_2O_7$ are set forth in Table 1 below.

TABLE 1

| | $Hg_2Nb_2O_7$ (a = 10.453Å, x = 0.323) | | | $Cd_2Nb_2O_7$ (a = 10.372Å, x = 0.316) | | |
|---|---|---|---|---|---|---|
| h k l | $I/I_0$ | 2θ | d(Å) | $I/I_0$ | 2θ | d(Å) |
| 1 1 1 | 111.0 | 14.68 | 6.0350 | 2.5 | 14.79 | 5.9883 |
| 2 2 0 | 0.1 | 24.08 | 3.6957 | 0.0 | 24.27 | 3.6671 |
| 3 1 1 | 63.9 | 28.32 | 3.1517 | 1.3 | 28.54 | 3.1273 |

TABLE 1-continued

| h k l | Hg$_2$Nb$_2$O$_7$ (a = 10.453Å, x = 0.323) | | | Cd$_2$Nb$_2$O$_7$ (a = 10.372Å, x = 0.316) | | |
|---|---|---|---|---|---|---|
| | I/I$_0$ | 2Θ | d(Å) | I/I$_0$ | 2Θ | d(Å) |
| 2 2 2 | 1000.0 | 29.60 | 3.0175 | 1000.0 | 29.84 | 2.9941 |
| 4 0 0 | 347.5 | 34.31 | 2.6133 | 309.7 | 34.59 | 2.5930 |
| 3 3 1 | 95.5 | 37.50 | 2.3981 | 41.3 | 37.81 | 2.3795 |
| 4 2 2 | 2.4 | 42.36 | 2.1337 | 4.9 | 42.71 | 2.1172 |
| 5 1 1 | 41.1 | 45.07 | 2.0117 | 11.3 | 45.44 | 1.9961 |
| 3 3 3 | 1.0 | 45.07 | 2.0117 | 4.2 | 45.44 | 1.9961 |
| 4 4 0 | 417.7 | 49.31 | 1.8478 | 414.7 | 49.73 | 1.8335 |
| 5 3 1 | 33.5 | 51.74 | 1.7669 | 3.3 | 52.17 | 1.7532 |
| 4 4 2 | 0.0 | 52.53 | 1.7422 | 0.0 | 52.95 | 1.7287 |
| 6 2 0 | 1.3 | 55.61 | 1.6528 | 3.7 | 56.08 | 1.6400 |
| 5 3 3 | 6.8 | 57.84 | 1.5941 | 0.2 | 58.34 | 1.5817 |
| 6 2 2 | 386.2 | 58.58 | 1.5758 | 369.1 | 59.08 | 1.5636 |
| 4 4 4 | 96.8 | 61.45 | 1.5088 | 94.3 | 61.99 | 1.4971 |
| 5 5 1 | 3.7 | 63.56 | 1.4637 | 0.4 | 64.12 | 1.4524 |
| 7 1 1 | 10.4 | 63.56 | 1.4637 | 1.0 | 64.12 | 1.4524 |
| 6 4 2 | 0.1 | 66.99 | 1.3968 | 0.4 | 67.59 | 1.3860 |
| 5 5 3 | 7.9 | 69.01 | 1.3609 | 1.0 | 69.63 | 1.3503 |
| 7 3 1 | 6.0 | 69.01 | 1.3909 | 0.4 | 69.63 | 1.3503 |
| 8 0 0 | 54.0 | 72.31 | 1.3066 | 52.5 | 72.97 | 1.2965 |
| 7 3 3 | 11.2 | 74.27 | 1.2770 | 4.0 | 74.94 | 1.2671 |
| 6 4 4 | 0.0 | 74.91 | 1.2676 | 0.0 | 75.60 | 1.2578 |
| 6 6 0 | 0.6 | 77.48 | 1.2319 | 1.6 | 78.20 | 1.2224 |
| 8 2 2 | 1.0 | 77.48 | 1.2319 | 1.7 | 78.20 | 1.2224 |
| 7 5 1 | 8.3 | 79.39 | 1.2070 | 0.8 | 80.13 | 1.1977 |
| 5 5 5 | 2.7 | 79.39 | 1.2070 | 0.8 | 80.13 | 1.1977 |
| 6 6 2 | 137.0 | 80.02 | 1.1990 | 128.0 | 80.77 | 1.1897 |
| 8 4 0 | 116.4 | 82.54 | 1.1687 | 109.2 | 83.33 | 1.1596 |

The exact intensities of the peaks in an observed powder X-ray diffraction pattern vary in a way which depends on the details of the stoichiometry. The differences are most sensitive to differences in the atomic number of the A and B cations. The examples in Table 1 are illustrative of cases where the difference in atomic number is large (Hg$_2$Nb$_2$O$_7$) and smaller (Cd$_2$Nb$_2$O$_7$).

Use of these mixed metal oxide catalysts having the pyrochlore structure in the process of the present invention preferably includes the following operating conditions. In a preferred embodiment the process is carried out at a temperature generally between about 500° C. and 900° C., but in a more general sense the process could be operated in a range of 300° C. to 1200° C., depending upon the particular hydrocarbon stream and/or products desired therefrom. The total gaseous pressure present within the reactor is preferably above 1 atmosphere, but less than about 100 atmospheres, and more preferably between about 1 and 30 atmospheres. When an oxidizing gas is used in the reactor, that oxidizing gas will generally contain molecular oxygen, although other gases such as steam, nitrogen or carbon oxides may also be present therein. The preferred oxygen-containing gases are air and oxygen, with air being particularly preferred. The same holds true when not co-feeding the oxidizing gas the hydrocarbon to the reactor but is used for regeneration of the catalyst. When co-feeding the oxidizing gas and the hydrocarbon, it is also preferred to maintain the volume ratio of hydrocarbon feedstock to oxygen fed to the reactor within the range of between about 0.1:1 to about 100:1, preferably within the range of about 1 to about 50:1. In general, the hydrocarbon feed and the added oxygen (or source of oxygen) can be diluted to reduce the partial pressures by the addition of a diluent gas, such as nitrogen or steam. The volume fraction of this diluent gas will generally be in the range of 0 to about 80 volume %, and preferably in the range of from about 7 to 67 volume %. The preferred hydrocarbon feedstock contains methane, preferably in a volume percent of from about 40 to 100%, more preferably between about 80 and 100%. A preferred source for this feedstock is natural gas. In other applications, however, the hydrocarbon feedstock can include higher hydrocarbons. In that case, the desired products are the dehydrogenation and oxidative coupling products. For example, by contacting the catalyst with ethane in an oxidizing gas one can provide ethylene as well as higher hydrocarbons. The space velocity of the feed stream used in these reactions should be sufficient to obtain the desired conversion of they hydrocarbon feedstock without sacrificing selectivity to useful products. Thus, optimum space velocities, while dependent upon temperature and pressure conditions, will typically be within the range of about 10 to 100,000 hr$^{-1}$, and preferably between about 600 and 40,000 hr$^{-1}$.

In accordance with another aspect of the present invention, among the mixed metal oxide compounds having the pyrochlore structure within the scope of those disclosed above, which is preferred for use in connection with this invention, is a novel compound in its own right. More particularly, this high surface area mixed metal oxide compound having the pyrochlore structure has the formula A$_2$B$_2$O$_7$ in which A is a divalent metal cation, and B is a metal cation selected from the group consisting of niobium, tantalum and mixtures thereof. Preferably the mixed metal cation A is a divalent metal cation such as lead, calcium or mixtures thereof. Another mixed metal oxide compound having the pyrochlore structure which is within the scope of those discussed above, and which is also a novel compound in its own right, is a high surface area mixed metal oxide compound having the pyrochlore structure and the formula A$_2$(Sn$_{2-y}$A$_y$)O$_{7-z}$ in which A is bismuth, lead or mixtures thereof, $0.0 \leq y \leq 1.0$; and $0.0 \leq z \leq 1.0$. Preferably, when A is bismuth, $0.0 < y \leq 1.0$, and $0.0 < z \leq 0.5$, and when A is lead, $0.0 < y \%23 1.0$, and z is 1. These compounds will preferably have a surface area greater than about 20 m$^2$/g, and more preferably greater than about 100 m$^2$/g.

The mixed metal oxides having the pyrochlore structure which can be used in accordance with the present invention can be produced by reacting together sources of metal cation A and metal cation B.

Sources of the metal cations A or B include compounds (including those soluble in aqueous and aqueous-based systems) of these cations and mixtures thereof.

The most preferred sources of metal cations A or B include soluble oxysalts or halides, such as nitrates, oxalates, acetates, citrates, chlorides, and bromides, and alkoxides such as ethoxide, methoxide and isopropoxide. In the case of the alkoxides, suitable solvents include organic alcohols, such as methanol, ethanol or glycol; organic esters, such as ethyl acetate and organic ketones, especially diketones, such as acetyl acetonate. When the source of the cation is an alkoxide, hydrocarbon solvents such as n-octane, cyclohexane and toluene may also be used. Compounds which can be made soluble by dissolution in acids or bases, such as hydrochloric acid and nitric acid or sodium or potassium hydroxide, are also preferred sources of metal cations A or B, and include oxides, carbonates and basic or hydroxycarbonates. The most highly preferred sources of metal cation A are carbonates and nitrates.

The most preferred sources of the B metal cations niobium and tantalum include the alkoxides, such as niobium ethoxide or tantalum ethoxide; the alkali metal niobates and tantalates, such as $M_8[Nb_6O_{19}]16\ H_2O$, where M is Na or K, and $M_7H[Ta_6O_{19}]x\ H_2O$, where M is Na, x is 16 and where M is K, x is 13. The most preferred sources of the A and B metal cations bismuth, lead and tin are the carbonates, chlorides and nitrates. Preferably, the ratio of A cations to B cations utilized in the reaction thereof is within the range of from about 5:1 to about 1:2. Most preferably, the ratio of A cations to B cations is in the range of from about 2:1 to about 1:1.1. The ratio of A cations to B cations in the reaction mixture may generally be appreciably higher than the ratio of A cations to B cations in the final pyrochlore product.

The solutions of A cations and B cations are prepared by combining the appropriate amount of the source of cation and with the source of cation B in a suitable reaction medium. When necessary in order to effect dissolution, the sources of metal cations A and B may be dissolved in an aqueous acid solution. Preferably, the acid solution should be just acidic enough to dissolve the sources of metal cations A and B. Particularly preferred acids for this purpose are nitric acid and hydrochloric acid. Alternatively the source of one of cation A and cation B may be made soluble in an aqueous base solution, such as sodium or potassium hydroxide.

Once these solutions have been prepared, the next steps in the preparation of the high surface area oxide compounds hereof is combination of the solutions of A cations and B cations and treatment of the resulting solution or suspension with an alkaline medium.

The alkaline medium so utilized includes any alkaline medium which will promote reaction between the A and B cations in the aqueous solution or suspension and which will thus cause formation of the desired pyrochlore compound. These alkaline media include aqueous solutions of alkali metal hydroxides. The alkaline medium is preferably an aqueous solution of a base selected from the group consisting of sodium hydroxide, potassium hydroxide, lithium hydroxide, rubidium hydroxide, ammonium hydroxide, tetra-alkyl (such as tetra-methyl) ammonium hydroxides, and mixtures thereof. Preferably, the pH of the alkaline medium is at least about 10.0. Most preferably, the pH of the alkaline medium is greater than about 13. Other alkaline media which can be employed include the aqueous mono-, di- and tri-alkyl or aryl amines, such as ethylamine, dimethylamine, trioctylamine and benzylamine.

The order of addition of the solution source of cations A and B and of the alkaline medium itself is not critical. However, all of the A and B cations should be exposed to an excess of alkaline medium.

The next step in the production of the mixed metal oxide compounds hereof, after preparation of the alkaline solution or suspension, includes heating of the alkaline solution of A and B cations at temperatures below about 250° C. Preferably, the temperature of the reaction mixture is less than about 150° C. Most preferably, the temperature of the reaction mixture is less than about 100° C.

The time period for this reaction to occur is that time period necessary for preparation of the mixed metal oxide product hereof having the pyrochlore structure from the alkaline solution. In general, the longer the reaction time period, the greater the amount of crystalline product obtained. A significant amount of reaction product is usually obtained after a reaction period of less than about one day. In general, a reaction time period of about one to seven days is satisfactory.

After completion of the reaction, the product may be separated by conventional separation techniques. These separation techniques include filtration and centrifugation. The product may also be treated by conventional post-treatment techniques. These post-treatment techniques include heat treatments to improve the crystallinity of the product and wash treatments to leach out unreacted components.

The above reaction conditions provide a product with the pyrochlore structure, and may, particularly in the case of the most preferred compounds hereof, provide such product with the pyrochlore structure having a high surface area, generally in the range of at least about 20 up to about 200 $m^2/g$, and preferably at least about 100 $m^2/g$. The pyrochlore oxides of this invention may be metastable phases which cannot be prepared by high temperature methods.

While the above procedure for production of the mixed meta oxides with the pyrochlore structure useful in the processes of the present invention is preferred, other methods may be used for preparing these catalysts. These additional processes include dry-mixing suitable starting materials in the appropriate proportions and then heating the mixture to high temperatures to effect that reaction. In this case the suitable starting materials include the oxides, oxysalts, such as nitrates, carbonates, citrates, acetates, or oxalates thereof, and the like. The appropriate portions relate to the final product being produced, and the process includes high temperatures of between about 300° C. and 1800° C., preferably between about 500° C. and 1200° C. In general, mixing is accomplished by grinding with a mortar and pestle or by ball milling the powders in dry form. Alternatively, before mixing, the powders can be slurried with a suitable non-reactive liquid, such as an organic hydrocarbon, alcohol, ketone or ether. In the latter case, the mixed slurry is dried at a temperature sufficient to remove the liquid before the high temperature part of the reaction process. In the reaction process itself, the mixed reactants are contained in a suitable nonreactive container or crucible. Suitable crucible materials include alumina, zirconia, magnesia, platinum and gold. The reactant powder may be heat treated as a loose powder, or alternatively it may be pressed into pellets. The powder may then be converted into the final product in a single step, but the total reaction time can often be reduced by interrupting the process, cooling the sample to room temperature, and regrinding it before continuing with the high temperature treatment.

In another embodiment of the present invention the mixed metal oxide catalysts hereof can be supported on a high surface area support which can be made by well-known methods. Suitable techniques for doing so include dry mixing the oxide catalyst with the support by a technique known as ball milling, and forming the oxide catalyst in the presence of the support by coprecipitation and subsequent calcination. Suitable such supports include silica, alumina, silica-alumina, silica-magnesia, titanium dioxide, magnesia, calcium oxide, zirconia, calcium zirconium oxide, yttrium zirconium oxide, and the like. Any such support which is inert and has a stable surface area and composition may be used in connection with these catalysts.

It is also possible to utilize these mixed metal oxide catalysts in conjunction with various known additives or promoters, as are well-known in this art. These promoters can thus include the alkali metals, such as lithium, sodium and potassium; the alkaline earth metals;

the halogens, such as chlorine and bromine; the oxyanions, such as the phosphates and borates; and mixtures thereof.

The synthesis of the pyrochlore compositions hereof, as well as the uses of these compounds as catalyst for the conversion of light hydrocarbons to higher hydrocarbons, is further illustrated by the examples below.

EXAMPLE 1

Synthesis of the Pyrochlore Compound $Pb_2Nb_2O_7$

An aqueous solution of $Pb(NO_3)_2$ (3.31 g, 50 ml) was combined with an ethanol solution of $Nb(OC_2H_5)_5$ (3.18 g, 50 ml) to provide a mixture having a 1:1 molar ratio of lead to niobium. A white precipitate was formed. The entire mixture was then combined with 300 ml of 2M KOH and the resulting suspension was heated in a sealed teflon container at 60° C. for 100 hours and then at 85° C. for 48 hours. The yellow product was separated by filtration, washed with water and dried at 110° C. in air for 2 hours. An X-ray diffraction pattern of the product showed the presence of only a pyrochlore phase with a pseudocubic lattice parameter of 10.65 Angstroms in good agreement with the literature value. The X-ray diffraction pattern showed considerable line broadening consistent with the surface area of 112 $m^2/g$ as measured by the Brunauer-Emmett-Teller nitrogen absorption method (BET). Elemental analysis gave Pb:Nb ratio of 0.97:1.0, which is in agreement with the anticipated pyrochlore composition.

EXAMPLE 2

Synthesis of the Pyrochlore Compound $Pb_2Ta_2O_7$

An aqueous solution of $Pb(NO_3)_2$ (3.31 g, 50 ml) was combined with an ethanol solution of $Ta(OC_2H_5)_5$ (4.06 g, 50 ml) to provide a mixture having a 1:1 molar ratio of lead to tantalum. A white precipitate was formed immediately. The mixture was combined with 200 ml of aqueous 2M KOH and reacted as described in Example 1 but for 112 hours at 100° C. The yellow product gave an X-ray powder pattern indicating the formation of a pure pyrochlore phase with a pseudocubic lattice parameter of 10.67 Angstroms in good agreement with the literature. The X-ray pattern showed considerable line broadening consistent with a measured BET surface area of 111 $m^2/g$. Elemental analysis gave a Pb:Ta ratio of 0.98:1.0, which is in agreement with the anticipated pyrochlore composition.

EXAMPLE 3

Synthesis of the Pyrochlore Compound $Ca_2Nb_2O_7$

An ethanolic solution of $Ca(NO_3)_2 \cdot 4 H_2O$ (1.08 g, 50 ml) was combined with an ethanolic solution of $Nb(OC_2H_5)_5$ (1.74 g, 50 ml). The resulting mixture was combined with 250 ml of aqueous 2M KOH and heated as described in Example 1 but for 114 hours at 100° C. After work up, an X-ray powder pattern of the white product showed only the presence of a pyrochlore phase with a cubic cell constant of 10.44 Angstroms. The surface area determined by the BET method was 152 $m^2/g$. Elemental analysis gave K:Ca:Nb ratios of 0.04:1.00:1.01 in agreement with the anticipated pyrochlore composition.

EXAMPLE 4

Synthesis of the Pyrochlore Compound $Ca_2Ta_2O_7$

An ethanolic solution of $Ca(NO_3)_2 \cdot 4 H_2O$ (2.36 g, 150 ml) was combined with an ethanolic solution of $Ta(OC_2H_5)_5$ (4.06 g, 100 ml). The resulting mixture was combined with 200 ml of aqueous 2M KOH and heated as described in Example 1 but for 72 hours at 82° C. and then for 120 hours at 100° C. After work up, an X-ray powder pattern of the white product showed the formation of a pure pyrochlore with a cubic lattice parameter of 10.42 Angstroms. The BET surface area of the product was 136 $m^2/g$.

EXAMPLE 5

Solution Synthesis of a Pyrochlore Compound Having the General Formula $Bi_2(Sn_{2-y}Bi_y)O_{7-z}$, Where $z = y/2$ An aqueous solution of $Bi(NO_3)_3 \cdot 5 H_2O$ (12.129 g, 100 ml water/30 ml concentrated nitric acid) was combined with solid tin chloride ($SnCl_4 \cdot 5 H_2O$ 8.763 grams) to provide a solution having a 1:1 mole ratio of bismuth to tin. The solution was then combined with 200 ml of 2M KOH. A white precipitate was formed. The pH was adjusted to 13 and the slurry was heated at 75° C. in a teflon container for 41 hours. The product was separated by filtration, washed with water and dried at 100° C. for 2 hours. An X-ray powder diffraction pattern of the product confirmed the presence of a crystalline phase with the pyrochlore structure and a pseudocubic lattice constant of 10.82Å. The surface area measured by the BET method was 77.6 $m^2/g$. The composition determined by elemental analysis was $Bi_2(Sn_{1.3}Bi_{0.7})O_{6.65}$, corresponding to a y value of 0.70.

EXAMPLE 6

Solution Synthesis of a Pyrochlore Compound $Bi_2(Sn_{2-y}Bi_y)_{7-y/2}$

An aqueous solution of $Bi(NO_3)_3 \cdot 5 H_2O$ (29.109 grams, 150 ml water/40 ml concentrated nitric acid) was combined with solid tin chloride ($SnCl_4 \cdot 5 H_2O$, 21.03 grams) to provide a solution having a 1:1 mole ratio of bismuth to tin. The solution was then combined with 500 ml of 2M KOH. A white precipitate was formed. The pH was adjusted to 13 and the slurry was heated at 100° C. in a teflon container for 113 hours. The product was separated by filtration, washed with water and dried at 100° C. for 16 hours. An X-ray powder diffraction pattern of the product confirmed the presence of a crystalline phase with the pyrochlore structure and a pseudocubic lattice constant of 10.760Å. The surface area measured by the BET method was 96.4 $m^2/g$. The composition determined by elemental analysis was $bi_2(Sn_{1.74}Bi_{0.26}O_{6.87}$, i.e., such that y has a value of 0.26.

EXAMPLE 7

Solution Synthesis of a Pyrochlore Compound $Pb_2(Sn_{2-y}Pb_y)O_6$

An aqueous solution of $Pb(NO_3)_2$ (19.871 grams, 150 ml water) was combined with solid tin chloride ($SnCl_4]5 H_2O$, 21.03 grams) to provide a slurry having a 1:1 mole ratio of lead to tin. The slurry was then combined with 500 ml of 2M KOH. The pH was adjusted to 12.8 and the slurry was heated at 100° C. in a teflon container for 113 hours. The product was separated by filtration, washed with water and dried at 100° C. for 2 hours. An X-ray powder diffraction pattern of the product confirmed the presence of a crystalline phase with a pyrochlore structure and a psuedocubic lattice constant of 10.699Å. The surface area measured by the BET method was 76 m$^2$/g. The composition determined by elemental analysis was Pb$_2$(Sn$_{1.70}$Pb$_{0.30}$)O$_6$, such that y had a value of 0.30.

EXAMPLE 8

Synthesis of a Pyrochlore Compound Sm$_2$Sn$_2$O$_7$

An aqueous solution of Sm(NO$_3$)$_3$·5 H$_2$O (4.264 grams, 50 ml water) was combined with a solution of tin chloride (SnCl$_4$·5 H$_2$O, 3.51 grams in 50 ml water) to provide a solution having a 1:1 mole ratio of samarium to tin. The solution was then combined with 200 ml of 1M KOH. A white precipitate was formed. The pH was adjusted to 9.5 and the slurry was heated at 100° C. in a teflon container for 113 hours. The product was separated by filtration, washed with water and dried at 100° C. for 16 hours. An X-ray powder diffraction pattern showed that the product was amorphous. The amorphous product was fired at 750° C. in air for 4.5 hours. An X-ray powder diffraction pattern of the product after this heat treatment confirmed the presence of a crystalline phase with the pyrochlore structure and a cubic lattice constant of 10.512Å. The surface area measured by the BET method was 167.5 m$^2$/g.

EXAMPLE 9

Solution Synthesis of a Pyrochlore Compound Bi$_2$(Ru$_{2-y}$Bi$_y$)O$_7$

An aqueous solution of Bi(NO$_3$)$_3$·5 H$_2$O (7.762 grams, 100 ml water/20 ml concentrated nitric acid) was combined with an aqueous solution of ruthenium nitrate (10.107 grams of an aquesou solution of Ru(NO$_3$)$_3$ containing 8% by weight of ruthenium as metal) to provide a solution having a 2:1 mole ratio of bismuth to ruthenium. The solution was then combined with 400 ml of 6M KOH. A thick black precipitate was formed and was heated at 100° C. in a teflon container for 112 hours. The product was separated by filtration, washed with water and dried at 100° C. for 2 hours. An X-ray powder diffraction pattern of the product confirmed the presence of a crystalline phase with the pyrochlore structure and a cubic lattice constant of 10.623Å. The surface area measured by the BET method was 92.4 m$^2$/g. The composition determined by elemental analysis was Bi$_2$(Ru$_{1.26}$Bi$_{0.74}$)O$_7$, such that y had a value of 0.74.

EXAMPLE 10

Solution Synthesis of a Pyrochlore Compound K$_{2-y}$Sn$_y$Ta$_2$O$_{7-z}$

A solution of tin chloride (SnCl$_2$ 1.896 grams, 50 ml of dry ethanol) was combined with an ethanolic solution of tantalum ethoxides ((Ta(OC$_2$H$_5$)$_5$ 4.06 grams in 50 ml of dry ethanol) to provide a solution having a 1:1 mole ratio of tin to tantalum. The solution was then combined with 200 ml of 2M KOH. A thick white precipitate was formed and the pH was adjusted to 13.5. The slurry was heated to 100° C. in a teflon container for 112 hours. The product was separated by filtration, washed with water and dried at 100° C. for 2 hours. An X-ray powder diffraction pattern of the product confirmed the presence of a crystalline phase with the pyrochlore structure and a cubic lattice constant of 10.631Å. The surface area measured by the BET method was 56.6 m$^2$/g. The composition determined by elemental analysis was (K$_{1.76}$Sn$_{0.06}$)Ta$_2$O$_6$

EXAMPLE 11

Synthesis of a Pyrochlore Compound Bi$_2$Sn$_2$O$_7$ From the Component Oxides

Tin oxide (SnO$_2$, 1.507 grams) and bismuth oxide (Bi$_2$O$_3$, 2.330 grams) were mixed by grinding together in an agate mortar. The well mixed oxides were heated in an alumina crucible in air for 65 hours at 800° C. The product was reground and heated for a further 66 hours at 900° C. An X-ray powder diffraction pattern of the product confirmed the presence of a crystalline phase with the pyrochlore structure and tetragonal lattice constants of 21.284Å and 21.398Å. The surface area measured by the BET method was 2.3 m$^2$/g. The composition determined by elemental analysis was Bi$_2$Sn$_2$O$_7$.

EXAMPLE 12

Synthesis of a Supported Pyrochlore Compound Bi$_2$(Sn$_{2-y}$Bi$_y$)O$_{7-y/2}$ A pyrochlore compound Bi$_2$(Sn$_{1.74}$Bi$_{0.26}$)O$_{6.87}$ was prepared as described in Example 6. The pryochlore compound was then added to a slurry of silica in water (1.0 grams catalyst/3.0 grams Cabosil L-90 in 100 ml water). The resulting slurry was then rotoevaporated to dryness under vacuum at 80° C. The product was finally dried at 100° C. for 18 hours. An X-ray powder diffraction pattern of the product confirmed the presence of two phases: a crystalline phase with the pyrochlore structure having a pseudo-cubic lattice parameter of 10.706Å, and an amorphous silica phase. The surface area of the supported catalyst, measured by the BET method was 93.2 m$^2$/g.

EXAMPLE 13

Synthesis of a Promoted Pyrochlore Compound Bi$_2$Sn$_2$O$_7$

A pyrochlore compound Bi$_2$Sn$_2$O$_7$ was prepared as described in Example 11. The pyrochlore compound was then added to a solution of KOH (0.06 grams KOH in 5 ml water), slurried, and the mixture allowed to dry at 125° C. for 21 hours. An X-ray powder diffraction pattern of the product confirmed the presence of a crystalline phase with the pyrochlore structure and tetragonal lattice constants of 21.280Å and 21.483Å. The product composition determined by elemental analysis indicated the presence of 0.5 moles of potassium per mole of Bi$_2$Sn$_2$O$_7$.

EXAMPLE 14

Synthesis of a Pyrochlore Compound K(NbW)O$_6$ From The Component Oxides

Potassium tungstate (K$_2$WO$_4$, 3.327 grams), niobium oxide (Nb$_2$O$_5$, 2.658 grams), and tungsten oxide (WO$_3$ 2.319 grams) were mixed by grinding together in an agate mortar. The well mixed oxides were heated in an alumina crucible in air for 86 hours at 600° C. The product was reground and heated for a further 20 hours at 600° C., then 20 hours at 600° C. and finally 19 hours at 650° C. with intermediate grindings. An X-ray powder diffraction pattern of the product confirmed the presence of a crystalline phase with the pyrochlore structure and a cubic lattice constant of 10.501Å. The surface area measured by the BET method was 2.9 m$^2$/g. The composition determined by elemental analysis gave K:Nb:W ratios of 0.94:0.99:1.0.

EXAMPLE 15

Synthesis of a Pyrochlore Compound (PbTl)Nb₂O₆.₅ From The Component Oxides

Thallium oxide ($Tl_2O_3$, 5.327 grams), niobium oxide ($NbO_2$, 5.827 grams), and lead oxide (PbO, 5.206 grams) were mixed by grinding together in an agate mortar. The well-mixed oxides were sealed in a quartz tube under vacuum and heated for 72 hours at 600° C. The quartz tube was opened and the product was reground. The reground product was resealed in a new quartz tube and heated for a further 72 hours at 600° C. An X-ray powder diffraction pattern of the product confirmed the presence of a crystalline phase with the pyrochlore structure and a cubic lattice constant of 10.61Å. The surface area measured by the BET method was 2.4 m²/g. The composition determined by elemental analysis gave a Pb:Tl:Nb ratio of 1.01:0.91:2.0.

EXAMPLE 16

Oxidative Coupling of Methane

Pyrochlore compounds $Pb_2Nb_2O_7$ and $Pb_2Ta_2O_7$, prepared as described in Examples 1 and 2, were used to catalyze oxidative coupling of methane to form higher hydrocarbons in the following experiments.

A charge of the catalyst (approximately 2 g, 50–80 mesh) was loaded into a 5 mm diameter vertical quartz reactor. The catalyst was supported in the reactor with quartz wool. A mixture of methane, oxygen and argon were flowed through the reactor at a total flow rate of 152 standard cc/minute at a total pressure of one atmosphere. The methane and oxygen partial pressures were 0.25 and 0.125 atmosphere, respectively ($CH_4$: $O_2$, 2.0: 1.0). The catalytic reactions were carried out in the temperature range of from about ambient to about 900° and the products were analyzed by gas chromatography. Both of the above referenced oxide catalysts were found to be active and selective for methane coupling as shown by the results in Table 2.

Conversion of methane is given by the formula:

$$\text{Conversion} = 1 - [F(CH_4)^{final} / F(CH_4)^{initial}],$$

where $F(CH_4)^{initial}$ is the flow rate of methane in grams/minute in the feed, and $F(CH_4)^{final}$ is the flow rate of methane in the product stream.

The selectivity is given by the following relation:

$$\text{Selectivity} = [k_i F(C_n H_m(i))^{final}] / [F(CH_4)^{initial} - F(CH_4)^{final}],$$

where the sum is over all desired hydrocarbon products with $n \geq 2$ and $m \geq 2$ (not CO and $CO_2$) and $F(C_nH_m)$ final is the flow rate in grams/minute of hydrocarbon product i in the product stream.

TABLE 2

| Catalyst | Temperature | CH₄ Conversion % | HC Selectivity % |
|---|---|---|---|
| Pb₂Nb₂O₇ (2.20 g) | 807° C. | 26.3 | 43.2 |
|  | 800° C. | 19.5 | 40.3 |
|  | 798° C. | 17.4 | 38.4 |
| Pb₂Ta₂O₇ (1.64 g) | 799° C. | 11.5 | 49.5 |
|  | 803° C. | 10.8 | 53.0 |
|  | 800° C. | 9.5 | 53.1 |

Furthermore, similar tests carried out for the pyrochlore compounds prepared and described in Examples 3–15 were also used to catalyze oxidative coupling of methane to form higher hydrocarbons in a similar experiment, and the results thereof are shown in Table 2 (with the conversion selectivities averaged for the runs actually carried out.)

TABLE 3

| Ex. # | Compound | Wt. (gms.) | CH₄ Conversion % 800° C. | CH₄ Conversion % 900° C. | HC Selectivity % 800° C. | HC Selectivity % 900° C. |
|---|---|---|---|---|---|---|
| 3 | Ca₂Nb₂O₇ | 0.50 | 31.0 | 35.1 | 16.0 | 18.8 |
| 4 | Ca₂Ta₂O₇ | 0.88 | 31.4 | 33.6 | 20.9 | 17.5 |
| 5 | Bi₂(Sn₁.₃Bi₀.₇)O₆.₆₅ | 1.03 | 6.1 | 19.0 | 74.0 | 72.4 |
| 6 | Bi₂(Sn₁.₇₄Bi₀.₂₆)O₆.₈₇ | 0.65 | 19.3 | 25.8 | 22.0 | 47.8 |
| 7 | Pb₂(Sn₁.₇₁Pb₀.₂₉)O₆ | 1.11 | 29.3 | 33.5 | 25.3 | 38.9 |
| 8 | Sm₂Sn₂O₇ | 0.43 | 27.1 | 30.6 | 4.9 | 8.4 |
| 9 | Bi₂(Ru₂₋ₓBiₓ)O₇ | 2.55 | 23.8 | — | 18.4 | — |
| 10 | (K₁.₇₆Sn₀.₀₆)Ta₂O₆ | 0.72 | 29.1 | 38.3 | 25.3 | 43.9 |
| 11 | Bi₂Sn₂O₇ | 0.30 | 5.5 | 33.6 | 40.3 | 40.4 |
| 12 | Bi₂(Sn₁.₇₄Bi₀.₂₆)O₆.₈₇ | 0.49 | 17.7 | 35.2 | 26.9 | 30.7 |
| 13 | Bi₂Sn₂O₇ | 0.32 | 9.2 | 19.4 | 29.5 | 54.1 |
| 14 | K(NbW)O₆ | 0.80 | 0.8 | 7.4 | 50.4 | 55.8 |
| 15 | PbTlNb₂O₆.₅ | 1.10 | 5.9 | 17.0 | 58.1 | 70.0 |

EXAMPLE 17

Oxidative Dehydrogenation and Coupling of Ethane

A bismuth-tin pyrochlore oxide prepared as described in Example 5 was used to catalyze the oxidative dehydrogenation and coupling of ethane to form ethylene and higher hydrocarbons in the following experiment.

A charge of the catalyst (1.06 grams, 50–80 mesh) was loaded into a 6 mm diameter vertical quartz reactor. The catalyst was supported in the reactor on quartz wool. A mixture of ethane, oxygen and argon was flowed through the reactor at a total flow rate of 80 standard cc/minute at a total pressure of 1 atmosphere. The ethane and oxygen partial pressures were 0.25 and 0.125 atmospheres, respectively. The catalytic reaction was carried out at 849° C. and the products analyzed by gas chromatography.

The catalyst was found to be active and selective for the oxidative dehydrogenation and coupling of ethane to form ethylene and higher hydrocarbons, 87.0% of the ethane was converted with a selectivity to ethylene and higher hydrocarbons of 70.0%. The conversion of ethane is given by the formula:

$$\text{Conversion} = 1 - [F(C_2H_6)^{final} / F(C_2H_6)^{initial}]$$

where $F(C_2H_6)$ initial is the flow rate of ethane in the feed in grams/minute; and $F(C_2H_6)^{final}$ is the flow rate of ethane in grams/minute in the product stream.

The selectivity is given by the relation:

$$\text{Selectivity} = [\Sigma F(C_nH_m(i))^{final}]/[F(C_2H_6)^{initial} - F(C_2H_6)^{final}]$$

where the sum is over all desired hydrocarbon products with $n \geq 2$ and $m \geq 2$ (except for the case $n = 2$ and $m = 6$ and not CO and $CO_2$) and $F(C_nH_m)(i)^{final}$ is the flow rate in grams/minute of hydrocarbon product i in the product stream.

As these and other variations, combinations and modifications of the features described above can be utilized without departing from the spirit of this invention, the foregoing description of the preferred embodiments should be taken by way of illustration rather than by way of limitation of the invention as defined in the claims.

What is claimed is:

1. An oxide compound with a pyrochlore structure and a surface area greater than about 20 $m^2/g$ having the formula $A_2B_2O_7$ wherein A is a divalent metal catio and B is a metal cation selected from the group consisting of niobium, tantalum and mixtures thereof.

2. The compound of claim 1 wherein said metal cation A comprises a divalent metal cation selected from the group consisting of lead, calcium, and mixtures thereof.

3. The compound of claim 1 wherein said metal A is lead and said metal cation B is niobium.

4. The compound of claim 1 wherein said metal cation A is calcium and said metal cation B is niobium.

5. The compound of claim 1 wherein said metal cation A is lead and said metal cation B is tantalum.

6. The compound of claim 1 wherein said metal cation A is calcium and said metal cation B is tantalum.

7. The compound of claim 1 having a surface area greater than about 100 $m^2/g$.

* * * * *